United States Patent [19]

Weyl

[11] Patent Number: 5,073,247

[45] Date of Patent: Dec. 17, 1991

[54] MEASURING SENSOR OF OXYGEN CONTENT OF HOT GAS WITH SPECIALLY SHAPED PROTECTIVE TUBE

[75] Inventor: Helmut Weyl, Schwieberdingen, Fed. Rep. of Germany

[73] Assignee: Robert Bosch GmbH, Stuttgart, Fed. Rep. of Germany

[21] Appl. No.: 651,767

[22] Filed: Feb. 7, 1991

[30] Foreign Application Priority Data

Mar. 28, 1990 [DE] Fed. Rep. of Germany ....... 4009890

[51] Int. Cl.[5] ............................................ G01N 27/26
[52] U.S. Cl. .................................. 204/428; 204/427; 204/424; 204/153.18
[58] Field of Search ...................... 204/424, 427, 153.8, 204/428; 338/34

[56] References Cited

U.S. PATENT DOCUMENTS

| | | |
|---|---|---|
| 4,199,424 | 4/1980 | Teitelbaum . |
| 4,339,320 | 7/1982 | Friese et al. . |
| 4,356,065 | 10/1982 | Dietz ................................ 204/153.1 |
| 4,362,609 | 12/1982 | Sano et al. ........................... 204/428 |
| 4,668,477 | 5/1987 | Nishio et al. ........................ 204/428 |
| 4,756,885 | 7/1988 | Raff et al. ............................ 204/428 |
| 4,842,713 | 6/1989 | Stahl .................................... 204/427 |
| 4,883,643 | 11/1989 | Nishio et al. ......................... 204/428 |

FOREIGN PATENT DOCUMENTS

| | | |
|---|---|---|
| 0187785 | 10/1988 | European Pat. Off. ............... 27/56 |
| 2805598 | 8/1979 | Fed. Rep. of Germany ...... 204/428 |
| 1518943 | 7/1978 | United Kingdom ................... 27/12 |

Primary Examiner—John Niebling
Assistant Examiner—Bruce F. Bell
Attorney, Agent, or Firm—Frishauf, Holtz, Goodman & Woodward

[57] ABSTRACT

A protective tube of metal resistant to corrosion from hot gas surrounds and is spaced from a closed-end ceramic sensor body within which is an electrical heater. The protective tube extends beyond the end of the sensor body and has an annular groove at its open end, which bulges into the space enclosed by the tube and the outer end of which provides a flange perpendicular to the axis of the tube a fine metal screen may be provided across the open end of the tube for incepting droplets of water that may sometimes be present in the gas to be measured. The open end of the protective tube may be only slightly constricted by the groove or, in another embodiment, it may taper down in a rounded fashion to a narrower opening.

12 Claims, 1 Drawing Sheet

MEASURING SENSOR OF OXYGEN CONTENT OF HOT GAS WITH SPECIALLY SHAPED PROTECTIVE TUBE

This invention concerns a measuring sensor for determining the oxygen content of gases, which is capable of use with hot gases, for example in the exhaust system of a motor vehicle. More particularly it concerns a measuring sensor having a tubular metal casing which in its interior holds and at least partly surrounds tightly a longitudinal section of a sensor element and/or a carrier therefor, both consisting essentially of ceramic material. The sensor element and/or its carrier protrude out of the interior of the metal casing in a direction towards a flow of gas to be measured and are surrounded in the region of that protrusion by a protective tube, spaced from the sensor element. The protective tube is connected by a tight connection to the metal casing at one end and at the other end is open and is so disposed that gas must be deflected by about 90° in direction out of the gas flow in order to reach the sensor element.

A measuring sensor of the kind just described is already known from European Patent No. 0 187 785 and German Patent No. 25 40 030.

It is not of significance for the present invention what the measurement principle is by which the sensor element operates. For use in connection with the present invention, however, it is preferable to utilize sensor elements and/or carriers therefore which consist of ceramic material.

The function of the protective tube of such a measuring sensor is mainly to prevent the gases to be measured from impinging directly on the sensor element or its carrier. The direct incidence of the gas to be measured and of the particles contained in that gas on the sensor elements or their carriers impairs these components as a result of the aggressive hot gas temperature changes and also by mechanical damage from the particles contained in the gas.

Such damage is reduced by having the opening of the protective tube disposed essentially parallel to the gas flow, so that gas has to be deflected from that flow by about 90° to reach the sensor element, but this precaution has not been sufficient to prevent damage.

SUMMARY OF THE INVENTION

It is an object of the present invention to provide a sensor of the above-described kind in which impairment and damage of the sensor element and/or its carrier, especially when these are made of ceramic material, will be greatly reduced.

It has been found that it is important to prevent droplets of condensed water, which is one of the products of combustion in the hot gas, from reaching the heated sensor element or its carrier during the start-up of a vehicle motor.

Briefly, the protective tube is formed with a coaxially running external groove bulging into the interior of the protective tube, located right at the open end of the protective tube and terminating the open end as an outward flange of the tube. The protective tube is preferably made of metal. Additional coaxial grooves spaced from each other and bulging the metal inwards are helpful.

The invention has the advantage that during the warm-up phase of an internal combustion engine, turbulent water droplets in the exhaust gases do not reach the sensor element or its carrier As a result of the invention the operating reliability and useful life of measuring sensors of this kind are substantially improved. This advantage holds particularly for those measuring sensors in which the sensor element or its carrier is heated by an electrical heating element integrated within the sensor.

Preferably the profile radius of the one or more grooves, as measured on the exterior of the protective tube, is in the range from 0.5 to 3 millimeters. In one embodiment in which there is just one groove near the open end of the protective tube, the width of the flange-like termination of the groove and of the protective tube is in the range from 1.5 to 5 mm.

In another embodiment the open end of the protective tube is preceded by a portion of the tube in which the diameter diminishes towards the opening. This portion is preferably of curved profile. The clear aperture of the open end in this last mentioned embodiment is preferably in the range between 2 and 7 millimeters and most preferably about 5 millimeters. In order to avoid drops of moisture in turbulences of the gas flow from getting to the sensor element, it is preferable to provide a fine-mesh metal grid or sieve across the opening at the open end of the protective tube.

BRIEF DESCRIPTION OF THE DRAWINGS

The invention is further described by way of illustrative examples with reference to the annexed drawings, in which.

DESCRIPTION OF THE ILLUSTRATED EMBODIMENTS

Figure 1:
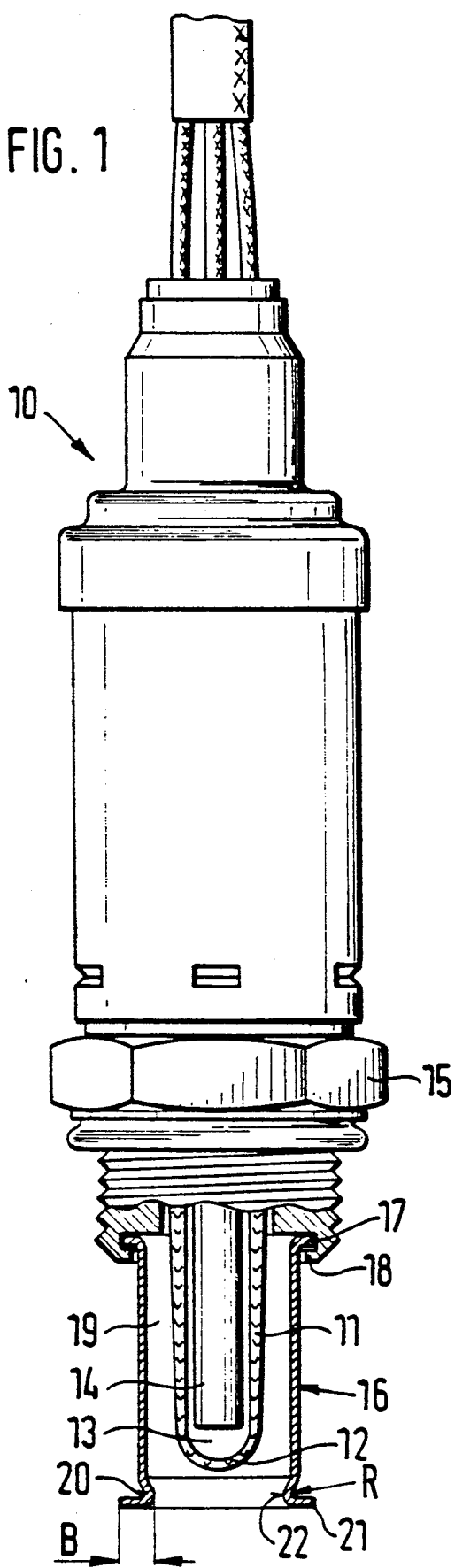
FIG. 1 is a side view of a measuring sensor according to the invention in which the end portion, part of which projects into the gas to be measured, is shown in longitudinal section.

FIG. 1 shows a measuring sensor 10 for the determination of oxygen content of gases which is particularly suited for use in exhaust gases of internal combustion engines and is designed for being mounted on an exhaust gas pipe. The basic construction of such a measuring sensor, which in the illustrated example functions according to the known principle of the oxygen concentration chain with an ion-conducting solid electrolyte, includes a solid electrolyte tube 11 terminating in a bottom 12 at its end facing the gas to be measured Within the internal space 13 of the solid electrolyte tube 11 is a rod-shaped electrical heating element 14. The construction so far described is already known from German Utility Model 81 01 584.

The solid electrolyte tube 11 has thin electrode layers (for example of platinum) on its outer and inner surfaces which are not shown in FIG. 1 and it also in part bears protective layers. The solid electrolyte tube 11 itself consists of ceramic material.

In place of the sensor element just described there could also be used plate-shaped sensor elements or sensor element carriers, which likewise consist of ceramic material or contain ceramic structural components. Such other sensors need not necessarily operate according to the above-mentioned principle of the oxygen concentration chain with ion-conducting solid electrolyte. They could also have other operative mechanicms, as for example sensors whose electrical resistance change with changing gas content in the gas to be measured (German patent 25 40 030) or sensors which have ion-conducting solid electrolytes but operate according to the polarographic measurement principle (published German patent application DE OS 27 11 880). The present invention is therefore not dependent upon the system of the measuring process, but is concerned with the structure of those measuring sensors in which ceramic components are exposed to the gases to be measured.

The portion of the solid electrolyte tube 11 which projects out of the metal casing 15 of the measuring sensor 10 is surrounded, but spaced from, a protective tube 16 which preferably consists of a metal which is resistant to corrosion from hot gases. This protective tube 16 has an outwardly directed flange 17 at its end remote from the gas entry. That flange is formed in the shape of a rolled annular disk and is fastened to the end surface of the metal casing 15 by means of a beaded edge 18. Instead of this method of fastening the protective tube to the metal casing other known fastening processes can also be used.

The protective tube 16 usually has a total length of about 20 millimeters, but it may, according to the particular application, have a length between 12 and 30 millimeters, preferably between 18 and 25 millimeters. The projecting end section of the protective tube 16 extends beyond the end of the solid electrolyte tube 11 by at least 2 to 3 millimeters. In order to reach the sensor element of the measuring sensor 10, the gas to be measured must therefore change its direction of flow by about 90°. According to the invention, this protective tube 16 has, right at its free end, a coaxially running groove 20 bulging into the internal space 19, which turns away from the interior space 19 of the protective tube in the manner of a flange at the free end region 21 of the tube. The depth of the groove 20, measured on the outside of the protective tube 16 is between 0.5 and 3 millimeters, while the radius R resulting from the presence of the groove 20 also is between 0.5 and 3 millimeters. Preferably the free end region 21 produced by the presence of the groove has an annular width B of between 1.5 and 5 millimeters, measured from the inside of the opening 22 at the end of the tube 16 that projects into the measuring gas. As a result of this shaping of the open end of the protective tube 16 the water condensate from the combustion products contained in the gas to be measured is kept away from the ceramic material, thus preventing damage therefrom and impairment of the ceramic elements exposed to the gas.

Figure 2:
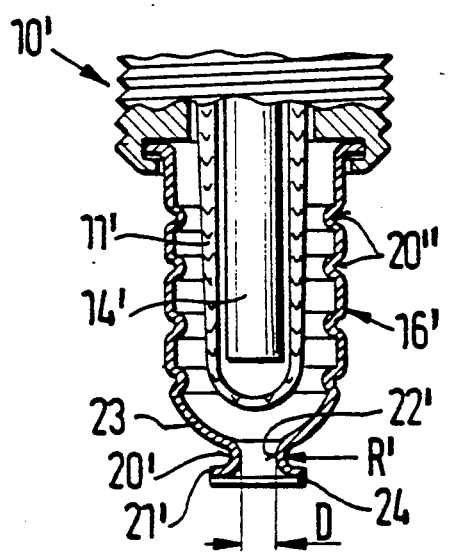
FIG. 2 is a longitudinal section through the end portion of another embodiment of measuring sensor according to the invention, both FIGS. 1 and 2 being magnified representations of the sensor structures.

FIG. 2 shows the gas-exposed end of a second embodiment 10' of a gas measurement sensor according to the invention, here shown, as in the case of FIG. 1, on a magnified scale. Again, although in this figure there is also shown a solid electrolyte tube 11' and a rod-shaped electrical heating element 14', another kind of sensor element having ceramic components could be used as mentioned in the introduction of this description.

The protective tube 16' of this measurement sensor 10' is of such shape that the longitudinal cross-section in the portion 23 near the open tube end has its diameter reduced, in funnel shape, towards the opening 22'. Its end portion exposed to the gas to be measured, again, has a groove 20' of which the free end region 21' leads away from the opening 22'. The diameter of the protective tube 16' which begins at it full value at its end connected to the metal casing 15' is so reduced at its other end that the opening 22' has a clear aperture of which the diameter D is between 2 and 7 millimeters, with a diameter D of about 5 millimeters being preferred for most applications The portion 23 where the diameter diminishes has been found to be most effective when it is of rounded shape as shown in FIG. 2.

The dimensions mentioned in connection with FIG. 1 regarding the radius R of the groove 20 and the free end region 21 of the groove or crease 20 apply correspondingly for the elements R' and 21' of the embodiment illustrated in FIG. 2.

It has been found that the objects of the invention are still better accomplished if the protective tube 16' has, in addition to the groove 20', at least two more grooves 20" over its length, and preferably four more grooves 20". These grooves 20" can be distributed evenly over the length of the protective tube 16', but they can, in accordance to the particular application, also be at different distances from each other, and they may be provided, in some cases, only in the region 23 of changing diameter The dimensions stated in connection with FIG. 1 regarding the radius R and the depth of the groove 20 apply correspondingly for these grooves 20".

For optimizing the manner of operation of the protective tube 16', i.e. in order to keep away from the ceramic portions of the measuring sensor such droplets of water as may be whirling around in the turbulence of the gas being measured, the opening 22' is covered with a fine-mesh sieve 24 made of metal which is resistant to corrosion by hot gas. This sieve 24, which is fastened, for example by welding, to the free end region 21' of the groove 20', may be made of wire of a diameter in the range from 0.5 to 1 millimeter to provide a mesh width between 0.2 and 0.8 millimeter, preferably about 0.4 millimeter. The protective tube 16' represents the optimal embodiment according to the invention.

Although the invention has been described with reference to particular illustrative embodiments, it will be understood that modifications and variations are possible within the inventive concept.

We claim:

1. A measuring sensor for determining the oxygen content of gases which is capable of use with hot gases, having a tubular metal casing which in its interior holds and at least partly surrounds tightly a longitudinal section of a sensor element, or a carrier therefor, or both a sensor element and a carrier therefor, said sensor element and said carrier therefor consisting essentially of ceramic material, said sensor element or said carrier therefor or both said sensor element and said carrier protruding out of the interior of said metal casing in a direction towards a flow of a gas to be measured, an, in the region of said protrusion, being surrounded in spaced relation by a protective tube which at its end section father from said gas flow is connected by a considerably tight connection to said metal casing and at its end nearer said gas flow extends beyond said sensor element or said carrier thereof or both said sensor element and said carrier, is open and is so disposed that gas of said gas flow must be deflected about 90° in direction out of said gas flow in order to reach said sensor element, characterized in that said protective tube (10,10') has no lateral openings and is formed with at least one coaxially running external groove (20, 20', 20") bulging into the interior of the protective tube, one said groove being located directly at said open end of said protective tube and terminating the open end of said tube as an outward flange of said protective tube.

2. A measuring sensor for determining the oxygen content of gases which is capable of use with hot gases, having tubular metal casing which in its interior holds and at least partially surrounds tightly a longitudinal section of a sensor element, or a carrier therefor, or both a sensor element and a carrier therefor, said sensor element and said carrier therefor consisting essentially of ceramic material, said sensor element, or said carrier therefor or both said sensor element and said carrier protruding out of the interior of said metal casing in the direction towards a flow of gas to be measured, and, in the region of said protrusion, being surrounded in spaced relation by a protective tube which at its end section farther from said gas flow is connected by a considerably tight connection to said metal casing and at its end nearer said gas flow extends beyond said sensor element or said carrier thereof or both said sensor element and said carrier, is open and is so disposed that gas of said gas flow must be deflected about 90° in direction out of said gas flow in order to reach said sensor element, characterized in that said protective tube (10, 10') is formed with at least one coaxially running external groove (20, 20', 20") bulging into the interior of the protective tube, the profile radius (r, R') of said at least one groove (20, 20') as measured on the exterior of said protective tube (10, 10') is in the range from 0.5 mm to 3 mm, one said groove being located directly at said open end of said protective tube and terminating the open end of said tube as an output flange of said protective tube.

3. The measuring sensor of claim 2, wherein an outward flange at the open end of said tube produced by said groove located at said open end of said tube has a width (B) which, as measured from the inside of the opening (22, 22') at the open end of said tube, is in the range from 1.5 mm to 5 mm.

4. The measuring sensor of claim 3, wherein said open end (22') of said tube has a portion of longitudinal cross-section (23) which reduces in diameter towards said opening at said open end of said protective tube.

5. The measuring sensor of claim 4, wherein said portion of said open end of protective tube having a cross-section in which the diameter is reduced towards said open end is of curved profile.

6. The measuring sensor of claim 4, wherein the minimum clear aperture of said open end of said protective tube has a diameter in the range between 2 mm and 7 mm.

7. The measuring sensor of claim 5, wherein the minimum clear aperture of said open end of said protective tube has a diameter in the range between 2 mm and 7 mm.

8. The measuring sensor of claim 6, wherein the minimum clear aperture of said open end has a diameter of about 5 mm.

9. The measuring sensor of claim 7, wherein the minimum clear aperture of said open end has a diameter of about 5 mm.

10. The measuring sensor of claim 1, wherein said protective tube (10, 10') is formed with at least two said coaxially running external grooves (20, 20', 20") bulging into the interior of said protective tube.

11. The measuring sensor of claim 10, wherein said protective tube is formed with at least three said coaxially running external grooves, and said grooves are separated from each other by respective spacings which differ from each other at least for the spacings on opposite sides of a groove.

12. A measuring sensor for determining the oxygen content of gases which is capable of use with hot gases, having a tubular metal casing which in its interior holds and at least partially surrounds tightly a longitudinal section of a sensor element, or a carrier therefor, or both a sensor element and a carrier therefor, said sensor element and said carrier therefor consisting essentially of ceramic material, said sensor element, or said carrier therefor or both said sensor element and said carrier protruding out of the interior of said metal casing in a direction towards a flow of gas to be measured, and, in the region of said protrusion, being surrounded in spaced relation by a protective tube which at its end section farther from said gas flow is connected by a considerably tight connection t said metal casing and at its end nearer said gas flow extends beyond said sensor element or said carrier thereof or both said sensor element and said carrier, si open and is so disposed that gas of said gas flow must be deflected about 90° in direction out of said gas flow in order to reach said sensor element, characterized in that said protective tube (10, 10') is formed with at least one coaxially running external groove (20, 20', 20") bulging into the interior of the protective tube, one said groove being located directly at said open end of said protective tube and terminating the open end of said tube as an output flange of said protective tube, and the open end of said protective tube has a single opening (22') which is covered by a metallic sieve (24).

* * * * *